United States Patent [19]

Chambers et al.

[11] Patent Number: 5,734,073
[45] Date of Patent: Mar. 31, 1998

[54] HALOGENATION REACTIONS

[75] Inventors: Richard Dickinson Chambers; Christopher John Skinner, both of Durham; Malcolm John Atherton; John Stewart Moilliet, both of Preston, all of United Kingdom

[73] Assignee: BNFL Fluorochemicals Ltd, Preston, England

[21] Appl. No.: 617,933

[22] PCT Filed: Jul. 24, 1995

[86] PCT No.: PCT/GB95/01738

§ 371 Date: Apr. 18, 1996

§ 102(e) Date: Apr. 18, 1996

[87] PCT Pub. No.: WO96/03356

PCT Pub. Date: Feb. 8, 1996

[30] Foreign Application Priority Data

Jul. 26, 1994 [GB] United Kingdom ............ 9414972

[51] Int. Cl.$^6$ ............ C07C 255/10; C07C 17/156; C07C 25/13

[52] U.S. Cl. ............ 558/425; 570/170; 570/174; 570/206; 570/207

[58] Field of Search ............ 558/425; 570/207, 570/206, 174, 170

[56] References Cited

U.S. PATENT DOCUMENTS 2,716,140  8/1955  McBee et al. ............ 260/648
4,621,160  11/1986 Desbois et al. ............ 570/207

OTHER PUBLICATIONS

Rozen et al J. of. Org. Chem. vol. 55, 1990 pp. 3552–3555.

Primary Examiner—Johann Richter
Assistant Examiner—Ebenezer Sackey
Attorney, Agent, or Firm—Sheridan Ross P.C.

[57] ABSTRACT

A method of halogenating an aromatic compound which comprises the steps of reacting an halogenating agent with the aromatic compound in the presence of fluorine and an acid, wherein the halogenating agent is at least one of an iodinating agent, a brominating agent and an chlorinating agent.

18 Claims, No Drawings

HALOGENATION REACTIONS

This application is a 371 of PCT/GB95/01738 filed Jul. 24, 1995.

FIELD OF THE INVENTION

The present invention relates to halogenation reactions, in particular to methods for the iodination or bromination or chlorination of aromatic compounds.

BACKGROUND AND SUMMARY OF THE INVENTION

Known procedures for the direct iodination of benzenoid compounds are limited. Some of the most effective known procedures involve the use of iodine in nitric acid, N-iodosuccinimide in triflic acid, decomposition of organomercurytrifluoroacetates in iodine-potassium iodide-dimethylformamide mixtures and iodine chloride. However, these procedures have a variety of limitations including inconvenience, limited reactivity and environmental unacceptability. Iodine fluoride has been made from iodine and fluorine and this provides a very effective iodinating agent. However, low temperatures have been required to produce the iodine fluoride.

According to the present invention there is provided a method of iodinating and/or brominating and/or chlorinating an aromatic compound which comprises the steps of reacting an iodinating agent and/or a brominating agent and/or chlorinating agent with the aromatic compound in the presence of elemental fluorine.

The iodinating agent may comprise elemental iodine or any one or more interhalogen compounds (such as ICl or IBr) and the brominating agent may comprise elemental bromine or one or more interhalogen compounds (such as BrF or $BrF_3$) and the chlorinating agent may comprise elemental chlorine or interhalogen compounds (such as ClF or $ClF_3$).

Surprisingly, we have now found that we can promote controlled iodination and/or bromination and/or chlorination of aromatic compounds by a method which can be simpler than, and does not possess the disadvantages of the prior art methods. The reaction may be carried out at ambient temperature, e.g. 20° C., and therefore no special heating or cooling steps are required. Furthermore, the yields obtained by the method according to the present invention may be greater than those obtained for prior art methods as illustrated hereinafter. Polyiodination and polybromination and polychlorination are easily achieved by simple adjustment of the stoichiometry of the reaction employed in the method.

The method according to the present invention may be carried out by passing fluorine gas into a liquid which contains the aromatic compound and the iodinating and/or brominating agent and/or chlorinating agent. The reaction may be carried out in a vessel in which the liquid is present or alternatively a flowing stream of the liquid may be contacted with a gaseous flow of fluorine in countercurrent fashion.

The said liquid may comprise a solvent for the aromatic compound and/or a solvent for the fluorine. If two or more solvents are employed these may or may not be miscible with one another.

The solvent for the aromatic compound may comprise an acid which may for example comprise an organic acid which may be a carboxylic acid such as formic acid, acetic acid or trifluoracetic acid or alternatively an inorganic acid such as sulphuric acid or trifluoromethanesulphonic acid or fluorosulphuric acid or hydrogen fluoride or antimony pentafluoride/hydrogen fluoride.

The solvent for the fluorine may comprise a fluorinated organic liquid such as a fluorinated alkane, e.g. $CF_2ClCFCl_2$ or a perfluorocarbon, e.g. a perfluoroalkane, or perfluorodecalin, or a fluorinated ether, or a perfluorinated ether or partly fluorinated systems such as a polyfluoroalcohol.

The present invention is suitable for the iodination or bromination or chlorination of a range of aromatic compounds. Thus, the aromatic compound which by the method of the present invention is iodinated or brominated or chlorinated is preferably benzene or naphthalene which may be substituted by from one to five substituents. Suitable substituents which may themselves be optionally substituted may be independently selected from: alkyl, alkoxy, halogen, —CN, —OH, —NO$_2$, —NH$_2$, —NHalkyl, —N(alkyl)$_2$, —NHCOalkyl, —COOalkyl, —COH, —COalkyl, —CONH$_2$, —CONH(alkyl)$_2$ COY, —CY$^1_3$ and SO$_2$Y$^2$, wherein Y is —H, —F, Cl, —Br, alkyl —OH or —Oalkyl $Y^1$ is F or Cl $Y^2$ is —F —Cl, —Br, —NH$_2$, NHalkyl, —N(alkyl)$_2$.

In each of these subsituents alkyl is preferably $C_{1-4}$ alkyl, alkoxy is preferably $C_{1-4}$ alkoxy and halogen is preferably —F or —Br or —Cl or —I.

When the aromatic compound is a substituted benzene it is preferably mono- or di-substituted. When benzene is disubstituted it is preferably substituted in the 1- and 4-positions. Preferred substituents for the aromatic compound are selected from —OH, —CN, NO$_2$, —NHCOH$_3$, —OCH$_3$, —COOH, —COCH$_3$, —COOCH$_3$, —CH$_3$, —F, —Cl, —Br, —I and —CONH$_2$ and combinations thereof.

The method according to the present invention generates an extremely electrophilic source for iodine or bromine or chlorine by a simple procedure. Control of the reaction is easily regulated by the rate of addition of fluorine to the reaction mixture.

Although it will normally be convenient to carry out the reaction provided by the method according to the present invention at ambient temperature, temperatures in the range –60° C. to +150° C. may be chosen, although those in the range –20° C. to +50° C. will normally be preferred.

The fluorine gas is preferably diluted before use by mixing with an inert gas such as nitrogen or helium. The concentration of fluorine in inert gas is preferably from 1% to 50% by volume, preferably from 2% to 25% by volume especially 5% to 15% by volume.

The ratio of fluorine to the aromatic compound may be varied within wide limits although it is preferred that the molar ratio is in the range 0.5 to 2.0:1, especially 1.1 to 1.25:1 (fluorine:aromatic compound).

The ratio of iodinating agent, brominating agent or chlorinating agent to the aromatic compound may be varied within wide limits although it is preferred that the molar ratio is in the range 0.5 to 8.0:1, especially 0.8 to 4.0:1 (halogenating agent:aromatic compound).

When fluorination is complete the halogenated product in the method according to the present invention may be isolated by purging the reaction mixture with inert gas to remove any residual fluorine gas and hydrogen fluoride followed by dilution with excess water or aqueous solution and extraction in a known way e.g. into a suitable solvent followed by distillation or crystallisation.

DETAILED DESCRIPTION OF THE INVENTION

Examples of iodo-derivatives which may be prepared by the method according to the present invention are listed in Table 1 as follows

TABLE 1

| Starting Material | Solvent | Product | C. Yield | Yield |
|---|---|---|---|---|
| 1,2,3,4-Tetrafluorobenzene | $H_2SO_4$ | 1,2,3,4-Tetrafluoro-5,6-diiodobenzene | — | 66% |
|  |  |  | — | 66% |
| 1,2,4,5-Tretrafluorobenzene | $H_2SO_4$/113 | 1,2,4,5-Tetrafluoro-5,6-diiodobenzene | — | 68% |
| 1,3,5-Trifluorobenzene | $H_2SO_4$ | 1,3,5-Trifluoro-2,4,6-triiodobenzene | 46% | 39% |
| 1,3,5-Trifluorobenzene | $H_2SO_4$/113 | 1,3,5-Trifluoro-2,4,6-triiodobenzene | 70% | 63% |
| 4,4'-Diflurobenzophenone | $H_2SO_4$ | 4,4'-Difluro-3,3'-diiodbenzophenone | 47% | 38% |
| Nitrobenzene | $H_2SO_4$/113 | 3-Iodonitrobenzene | 72% | 51% |
| α,α,α-Trifluorotoluene | $H_2SO_4$/113 | 3-Iodo-α,α,α-trifluorotoluene | 93% | 83% |
| 1,3-Bistrifluoromethylbenene | $H_2SO_4$/113 | 1,3-Bis-trifluoromethyl-5-iodobenzene | 89% | 83% |
| 4-Fluorobenzoic acid | $H_2SO_4$/113 | 4-Fluoro-3-iodobenzoic Acid 70% |  | 59% |
| 2,4-Difluorobenzoic Acid | $H_2SO_4$/113 | 2,4-Difluoro-iodobenzoic Acid 83% |  | 77% |
| 2,4-Difluoronitrobenzene | $H_2SO_4$/113 | 2,4-Difluoro-5-iodonitrobenene 94% |  | 84% |
| 4-Fluorobenzonitrile | $H_2SO_4$/113 | 4-Fluoro-3-iodobenzonitrile | 89% | 84% |
| 4-Fluoronitrobenzene | $H_2SO_4$/113 | 4-Fluoro-3-iodonitrobenzene | 95% | 79% |

In Table 1, the "113" indicates the solvent $CFCl_2CClF_2$, "$H_2SO_4$/113" indicates a mixture of the solvents $H_2SO_4$ and $CFCl_2CClF_2$ in the proportions 120 ml $H_2SO_4$ and 30 ml $CFCl_2CClF_2$. "C Yield" indicates calculated yield.

Examples of bromo-derivatives which can be prepared by the method according to the present invention are listed as follows in Table 2

TABLE 2

| Starting Material | Solvent | Product | Crude Yield | Yield |
|---|---|---|---|---|
| 4-Fluoronitrobenzene | $H_2SO_4$ | 3-Bromo-4-fluoronitrobenzene | 80% | 58% |
| 2,4-Difluoronitrobenzene | $H_2SO_4$ | 5-Bromo-2,4-difluoronitrobenene | 77% | 65% |
| 4-Fluorobenzoic Acid | $H_2SO_4$ | 3-Bromo-4-fluorobenzoic Acid | — | 65% |
| 2,4-Dinitrofluorobenzene | $H_2SO_4$ | 5-Bromo-2,4-dinitrofluorobenzene | 70% | 60% |

We have found that the method according to the present invention is a very effective halogenating method. For iodination, the method can give yields which are improved compared with the prior art. For example, in the prior art using iodine monofluoride nitrobenzene is not converted to 3-iodonitrobenzene. In contrast, 100% conversion can be achieved using the method according to the present invention.

Examples of procedures employed to prepare specific iodo- and bromo- and chloro-derivatives will now be described.

Experimental

In the following Examples $^1H$, $^{13}C$ and $^{19}F$ nmr spectra were recorded on a Varian VXR200, Bruker AC250, Varian VXR400S or a Bruker AC500; J values are given in Hz. Mass spectra were determined on a VG 7070E or a Fisons TRIO 1000 linked to a Hewlett Packard 5790A gas chromatograph fitted with a DB-624 capillary column. Fractional distillation was carried out using a Fischer Sahltroh MMS255 small concentric tube apparatus. Boiling points were recorded during distillation. Carbon, hydrogen and nitrogen elemental analysis were obtained using a Carbo Erba Strumentazione 1106 Elemental Analyser. Melting points measurements were carried out at atmospheric pressure and are uncorrected. Unless otherwise stated, chemicals were used as received from suppliers. Prior to the following halogenations, a passivated 3700 ml steel cylinder was charged with 2 atm of 50% fluorine in dry nitrogen (Air Products). This was then diluted with dry nitrogen to produce a 10% mixture of fluorine in dry nitrogen.

1. Iodination Reactions

In Examples 1 to 3 which follow the following general procedure was used.

A solution containing a polyfluorobenzene and iodine in 98% sulfuric acid (150 ml) was placed in a fluorination apparatus. Elemental fluorine (165 mmol) as a 10% mixture in nitrogen was then passed through the stirred solution using narrow bore polytetrafluoroethylene (PTFE) tubing at ca. 40 ml min$^{-1}$. After fluorination the mixture was poured into a 5% solution of sodium metabisulfite in ice (1500 ml), extracted with dichloromethane (3×100 ml) and then dried (MgSO$_4$). The dichloromethane was then removed under vacuum to leave an oil or solid which was then purified by distillation or recrystalisation (ethanol) to afford a single product.

EXAMPLE 1

5,6-Diiodo-1,2,3,4-tetrafluorobenzene 1,2,3,4-Tetrafluorobenzene(11.3 g, 75 mmol) and iodine (41.9 g, 165 mmol) gave 5,6-diiodo-1,2,3,4-tetrafluorobenzene (20 g, 66%); m.p. 48°–50° C. (lit.,[1] 50.5°–51.8° C.); (Found: C, 18.12; H, 0; N, 0. $C_6F_4I_2$ requires C, 17.93; H, 0; N, 0%); $\delta_F$ −102.4 (2F, AA'XX', $J_{AX}$22.5, $J_{AX'}$ −4.4, $J_{AA'}$ 19.2, $J_{XX'}$ 9.3, 2-F,3-F) and −151.2

(2F, AA'XX', $J_{AX}$ 22.5. $J_{AX'}$ -4.4, $J_{AA'}$ 19.2, $J_{XX'}$ 9.3, 1F, 4-F); $\delta_C$ 90.6 (2C, m, $^2J_{C-F}$ 24.4, 5-C, 6-C), 134.0 (2C, m, $^1J_{C-F}$ 260.0, 1-C,4-C) and 147.8 (2C, m, $J_{C-F}$ 247.0, 2-C, 3-C): m/z (EI⁺) 402 (M⁺, 100%).

EXAMPLE 2

1,3,5- Trifluoro-2,4,6-triiodobenzene 1,3,5-Trifluorobenzene(6.8 g, 51.5 mmol) and iodine(41.9 g, 165 mmol) gave 1,3,5-trifluoro-2,4,6-triiodobenzene(10.2 g, 39%): m.p. 143°–145° C.; (Found: C, 13.98; H, 0; N, 0. $C_6F_3I_3$ requires C, 14.14; H, 0; N, 0%); $\delta_F$ −69.0 (3F, s, 1-F,3-F, 5-F); $\delta_C$ 63.8 (3C, td, $^2J_{C-F}$ 34.5, $^4J_{C-F}$ 3.8, 2-C, 4-C, 6-C) and 162.2 (3C, dt, $^1J_{C-F}$ 243.8, $^3J_{C-F}$ 7.6, 1-C, 3-C, 5-C); m/z (EI⁺) 510 (M⁺, 30.8%).

EXAMPLE 3

4,4'-Difluoro-3,3'-diiodobenzophenone 4,4'-Difluorobenzophenone(16.4 g, 75.2 mmol) and iodine(41.9 g, 165 mmol) gave 4,4'-difluoro-3,3'-diiodobenzophenone(13.5 g, 38.3%); m.p. 129°–131° C.; (Found: C, 33.00; H, 1.22; N, 0. $C_{13}H_6F_2I_2O$ requires C. 33.22; H, 1.29; N, 0%); $\delta_H$ 7.18 (2H, dd, $^3J_{H-F}$ 8.4, $^3J_{H-H}$ 7.6, 5-H, 5-H'), 7.74 (2H, ddd, $^3J_{H-H}$ 8.5, $^4J_{H-F}$ 4.8, $^4J_{H-H}$ 2.0 6-H, 6-H') and 8.20 (2H, dd, $^4J_{H-F}$ 6.0, $^4J_{H-H}$ 2.0 2-H, 2-H'); $\delta_F$ −86.0 (2F, ddd, $^3J_{F-H}$ 7.2, $^4J_{F-H}$ 4.9 4-F, 4-F'); $\delta_C$ 81.8 (2C, d, $^2J_{C-F}$ 26.7, 3-C, 3-C') 115.7 (2C, d, $^2J_{C-F}$ 24.4, 5-C, 5-C'), 132.1 (2C, d, $^3J_{C-F}$ 8.8, 6-C, 6-C'), 141.2 (2C, d, $^4J_{C-F}$ 2.6, 2-C, 2-C'), 141.4 (2C, d, $^3J_{C-F}$ 3.1, 1-C, 1-C'), 164.4 (2C, d, $^1J_{C-F}$ 253.7, 4-C, 4-C') and 191.0 (1C, s, C=O); m/z (EI⁺) 470 (M⁺, 83.3%).

2. Use of Co-Solvents in Iodination Reactions

In Examples 4 to 14 which follow, the following general procedure was used.

A solution containing the aromatic compound to be iodinated and iodine in 98% sulfuric acid (120 ml) and 1,1,2-trichloro-1,2,2-trifluoroethane (30 ml) was placed in the fluorination apparatus. Elemental fluorine (165 mmol) as a 10% mixture in nitrogen was then passed through the stirred solution using narrow bore PTFE tubing at ca. 40 ml min⁻¹. After fluorination the mixture was poured into a 5% solution of sodium metabisulfite in ice (1500 ml), extracted with dichloromethane (3×100 ml) and then dried (MgSO₄). The dichloromethane was then removed under vacuum to leave an oil or solid which was then purified by distillation or recrystalisation (ethanol) to afford a single product.

EXAMPLE 4

5,6-Diiodo-1,2,3,4-tetrafluorobenzene 1,2,3,4-Tetrafluorobenzene(11.3 g, 75 mmol) and iodine (21.9 g, 86 mmol) gave 5,6-diiodo-1,2,3,4-tetrafluorobenzene (23 g, 76%).

EXAMPLE 5

1,2,4,5-Tetrafluoro-3,6-diiodobenzene 1,2,4,5-Tetrafluorobenzene(11.3 g, 75 mmol) and iodine (21.9 g, 86 mmol) gave 3,6-diiodo-1,2,4,5-tetrafluorobenzene (20.5 g, 68%); m.p. 109°–111° C. (lit;² 109°–111° C.); (Found: C. 17.59; H, 0; N, 0. $C_6F_4I_2$ requires C, 17.93; H, 0; N, 0%); $\delta_F$ −118.0 (4F, s,1-F, 2-F, 3-F, 4-F); $\delta_C$ 72.9 (2C, t, $^2J_{C-F}$ 27.9, 3C, 6-C) and 146.6 (4C, m, $^1J_{C-F}$ 250.4, 1-C, 2C, 4-C, 5-C); m/z (EI⁺) 402 (M⁺, 46.7%).

EXAMPLE 6

1,3,5-Trifluoro-2,4,6-triiodobenzene 1,3,5-Trifluorobenzene(6.9 g, 52.3 mmol) and iodine(21.9 g, 86 mmol) gave 1,3,5-trifluoro-2,4,6-triiodobenzene(16.6 g, 63%).

EXAMPLE 7

3-Iodonitrobenzene

Nitrobenzene(16.9 g, 137.5 mmol) and iodine (21.0 g, 82.7 mmol) gave 3-iodonitrobenzene (17.4 g, 51%); b.p. 116° C./1.5 mm (lit., 280° C.); (Found: C, 28.82; H, 1.54: N, 5.54. $C_6H_4INO_2$ requires C, 28.94; H, 1.62: N, 5.63%); $\delta_H$ 7.34 (1H, dd, $^3J_{H-H}$ 4.0, 5-H) 8.0 (1H, ddd, $^3J_{H-H}$ 7.8, $^4J_{H-H}$ 1.6, $^4J_{H-H}$ 1.0, 4-H), 8.17 (1H, ddd, $^3J_{H-H}$ 8.1, $^4J_{H-H}$ 2.2, $^4J_{H-H}$ 1.1, 6-H) and 8.45 (1H, t, $^4H_{H-H}$ 2.0, 2-H); $\delta_C$ 94.3 (1C, s, 3-C), 115.7 (1C, s, 6-C), 132.1 (1C, s, 5-C), 141.2 (1C, s, 2-C), 141.4 (1C, s, 4-C) and 164.4 (1C, s, 1-C); m/z (EI⁺) 249 (M⁺, 100%).

EXAMPLE 8

3-Iodo-α,α,α-trifluorotoluene

α,α,α-Trifluorotoluene(21.4 g, 144.5 mmol) and iodine (21.9 g, 86.2 mmol) gave 3-iodo-α,α,α-trifluorotoluene (32.6 g, 82.9%); b.p. 116° C./1.5 mm; (Found: C, 30.75; H, 1.40; N, 0. $C_7H_4F_3I$ requires C, 30.88: H, 1.47: N, 0%); $\delta_H$ 7.10 (1H, t, $^3J_{H-F}$ 8.4, $^3J_{H-H}$ 7.9, 5-H), 7.50 (1H, d, $^3J_{H-H}$ 7.8, 4-H), 7.7 (1H, d, $^3J_{H-H}$ 7.9, 6-H) and 7.9 (1H, s, 2-H); $\delta_F$ −86.0 (2F, ddd, $^3J_{F-H}$ 7.2, $^4J_{F-H}$ 4.9, 4-F); $\delta_F$ −69.2 (3F, s, CF₃); $\delta_C$ 94.5 (1C, s, 3-C), 123.5 (1C, q, $^1J_{C-F}$ 272.9, CF₃), 124.9 (1C, q, $^3J_{C-F}$ 3.6, 6-C), 130.8 (1C, s, 5-C), 132.8 (1C, q, $^2J_{C-F}$ 32.7, 1-C), 134.7 (1C, q, $^3J_{C-F}$ 3.8. 2-C) and 141.0 (1C, s, 4-C); m/z (EI⁺) 272 (M⁺, ?%).

EXAMPLE 9

1,3-Bis(trifluoromethyl)-5-iodobenzene

Bis-1,3-trifluoromethylbenzene(29.4 g, 137.5 mmol) and iodine (21.9 g, 86.2 mmol) gave bis-1.3-(trifluoromethyl)-5-iodobenzene (27.5 g, 83%); b.p. 58° C./26 mm; (Found: C. 28.00; H, 0.86; N, 0 $C_8H_3F_6I$ requires C, 28.24; H, 0.88; N ,0%); $\delta_H$ 7.9 (1H, s, 2-H) and 8.1 (2H, s, 4-H, 6-H); $\delta_F$ −63.7 (6F, s, CF₃); $\delta_C$ 94.2 (1C, s, 5-C), 122.2 (1C, m, $^3J_{C-F}$ 3.7, 2-C), 122.6 (2C, q, $^1J_{C-F}$ 273.1, CF₃), 133.5 (1C, q, $^2J_{C-F}$ 33.8, 1-C, 3-C) and 138.1 (1C, m, $^3J_{C-F}$ 3.4, 4-C, 6-C); m/z (EI⁺) 340 (M⁺, 76.3%).

EXAMPLE 10

4-Fluoro-3-iodobenzoic Acid

4-Fluorobenzoic acid(19.3 g, 137.5 mmol) and iodine (21.2 g, 83.5 mmol) gave 4-fluoro-3-iodobenzoic acid(21.4 g, 58.5%); m.p. 174°–176° C. (lit,³ 175°–176° C.); (Found: C, 31.52: H, 1.42: N, 0. $C_7H_4FIO_2$ requires C, 31.58; H, 1.50; N, 0%); $\delta_H$ 7.1 (1H, dd, $^3J_{H-H}$ 7.5, $^3J_{H-F}$ 8.6. 5-H), 7.0 (1H, ddd, $^3J_{H-H}$ 8.6. $^4J_{H-F}$ 4.9, $^4J_{H-H}$ 2.1, 6-H) and 8.5 (1H, dd, $^4J_{H-H}$ 2.2, $^4J_{H-F}$ 6.1, 2-H); $\delta_F$ −88.8 (1F, s, 4-F); $\delta_C$ 81.3 (1C, d, $^2J_{C-F}$ 26.6, 3-C), 115.8 (1C, d, $^2J_{C-F}$ 24.8, 5-C), 127.0 (1C, d, $^4J_{C-F}$ 3.3, 1-C), 132.6 (1C, d, $^3J_{C-F}$ 8.9, 6-C), 142.0 (1C, d, $^3J_{C-F}$ 3.3, 2-C), 165.2 (1C, d, $^1J_{C-F}$ 254.3, 4-C) and 169.8 (1C, s, C=O); m/z (EI⁺) 266 (M⁺, 100%)

EXAMPLE 11

2,4-Difluoro-5-iodobenzoic Acid 2,4-Difluorobenzoic acid(21.8 g, 137.5 mmol) and iodine (21.9 g, 86.2 mmol) gave 2,4-difluoro-5-iodobenzoic acid (29.9 g, 76.6%); m.p. 151°–152° C.; (Found: C, 29.61; H, 1.12; N, 0. $C_7H_3F_2IO_2$ requires C, 29.58: H, 1.06; N, 0%); $\delta_H$ 6.9 (1H, dd, $^3J_{H-F}$ 10.3, $^3J_{H-F}$ 7.6. 3-H) and 8.5 (1H, t, $^4J_{H-F}$ 7.4, 6-H); $\delta_F$ −81.3 (1F, m, 2-F) and −83.7 (1F, s, 4-F); $\delta_C$ 75.0 (1 C, dd, $^2J_{C-F}$ 26.5, $^4J_{C-F}$ 4.0, 5-C), 105.8 (1C, t, $^2J_{C-F}$ 27.3, 3-C),142.8 (1C, m, 6-C), 143.1 (1C, d, $^3J_{C-F}$ 3.8, 1-C), 163.6 (1C, dd, $^1J_{C-F}$ 266.4, $^3J_{C-F}$ 11.9, 2-C), 165.3 (1C, dd, $^1J_{C-F}$ 256.4, $^3J_{C-F}$ 12.3, 4-C) and 167.1 (1C, d, $^3J_{C-F}$ 3.4, C=O); m/z (EI⁺) 284 (M⁺, 100%)

EXAMPLE 12

2,4-Difluoro-5-iodonitrobenzene 2,4-Difluoronitrobenzene(21.1 g, 144.5 mmol) and iodine (21.9 g, 86.2 mmol) gave 2,4-difluoro-5-iodonitrobenzene (32.8 g, 83.6%); (Found: C, 25.10; H, 0.70; N, 4.91. $C_6H_2F_2INO_2$ requires C, 25.30; H, 0.70; N, 4.91%); $\delta_H$ 7.2 (1H, dd, $^3J_{H-F}$ 10.3, $^3J_{H-F}$ 7.8, 3-H) and 8.5 (1H, t, $^4J_{H-F}$ 7.2, 6-H); $\delta_F$ −78.8 (1F, s, 2-F) and −112.0 (1F, s, 4-F): $\delta_C$ 73.4 (1C, dd, $^2J_{C-F}$ 26.6, $^4J_{C-F}$ 4.6, 5-C), 105.0 (1C, dd, $^2J_{C-F}$ 29.5, $^2J_{C-F}$ 25.2, 3-C), 132.7 (1C, s, 1-C), 134.8 (1C, s, 6-C), 154.9 (1C, dd, $^1J_{C-F}$ 268.4, $^3J_{C-F}$ 12.3, 2-C) and 163.2 (1C, dd, $^1J_{C-F}$ 257.3, $^3J_{C-F}$ 11.4, 4-C); m/z (EI$^+$) 285 (M$^+$, 77.1%)

EXAMPLE 13

4-Fluoro-3-iodobenzonitrile

4-Fluorobenzonitrile(16.6 g, 137.5 mmol) and iodine (21.9 g, 86.2 mmol) gave 4-fluoro-3-iodobenzonitrile(28.5 g, 84%); m.p. 57°–59° C. (Found: C, 34.29; H, 1.18: N 5.64. $C_7H_3FIN$ requires C, 34.01; H, 1.21; N 5.67%); $\delta_H$ 7.2 (1H, m, 5-H), 7.0 (1H, m, 6-H) and 8.1 (1H, m, 2-H); $\delta_F$ −83.8 (1F, s, 4-F); $\delta_C$ 82.1 (1C, d, $^2J_{C-F}$ 27.5, 3-C), 110.3 (1C, d, $^4J_{C-F}$ 4.0, 1-C), 116.5 (1C, s, CN), 116.6 (1C, d, $^2J_{C-F}$ 25.4, 5-C), 134.3 (1C, d, $^3J_{C-F}$ 8.8, 6-C), 143.3 (1C, d, $^4J_{C-F}$ 3.2, 2-C) and 164.3 (1C, d, $^1J_{C-F}$ 255.0, 4-C); m/z (EI$^+$) 247 (M$^+$, 100%)

EXAMPLE 14

4-Fluoro-3-iodonitrobenzene

4-Fluoronitrobenzene(21.1 g, 144.5 mmol) and iodine (21.9 g, 86.2 mmol) gave 4-fluoro-3-iodonitrobenzene(25.7 g, 70%); (Found: C, 26.94; H, 1.09; N 5.24. $C_6H_3FINO_2$ requires C, 26.97; H, 1.12; N, 5.24%); $\delta_H$ 7.2 (1H, dd, $^3J_{H-H}$ 6.9, $^3J_{H-F}$ 9.0, 5-H), 8.3 (1 H, ddd, $^3J_{H-H}$ 9.1, $^4J_{H-F}$ 4.3, $^4J_{H-H}$ 2.8, 6-H) and 8.7 (1 H, dd, $^4J_{H-H}$ 2.8, $^4J_{H-F}$ 5.3, 2-H); $\delta_F$ −83.6 (1F, s, 4-F); $\delta_C$ 81.3 (1C, d, $^2J_{C-F}$ 28.6, 3-C), 116.0 (1C, d, $^2J_{C-F}$ 26.6, 5-C), 125.9 (1C, d, $^3J_{C-F}$ 9.3, 6-C), 135.2 (1C, d, $^3J_{C-F}$ 3.7, 2-C), 144.6 (1C, d, $^4J_{C-F}$ 1.8, 1-C) and 165.5 (1C, d, $^1J_{C-F}$ 265.2, 4-C); m/z (EI$^+$) 267 (M$^+$, 100%)

EXAMPLE 15

Iodination in Different Volumes of Co-Solvent

A solution containing nitrobenzene. (16.9 g, 137.5 mmol) and iodine (21.9 g, 86.2 mmol) in the required volumes of sulfuric acid and 1,1,2-trichloro-1,2,2-trifluoroethane was placed in the fluorination apparatus as used in the earlier Examples. Elemental fluorine (165 mmol) as a 10% mixture in nitrogen was then passed through the stirred solution at a rate of about 40 ml min$^{-1}$. After the fluorination, the mixture was poured into a 5% solution of sodium metabisulfite in ice (1500 ml), extracted with dichloromethane (3×100 ml) and then dried (MgSO$_4$). G.c./m.s. was used to determine the relative conversion. Removal of the dichloromethane under reduced pressure allowed determination of the crude yield.

EXAMPLE 16

Iodination in a Variety of Co-Solvents

A solution containing nitrobenzene (16.9 g, 137.5 mmol) and iodine (21.9 g, 86.2 mmol) in 98% sulfuric acid (75 ml) and the co-solvent (75 ml) was placed in the fluorination apparatus. Elemental fluorine (165 mmol) as a 10% mixture in nitrogen was then passed through the stirred solution at ca. 40 ml min$^{-1}$. After the fluorination the mixture was poured into a 5% solution of sodium metabisulfite in ice (1500 ml), extracted with dichloromethane (3×100 ml) and then dried (MgSO$_4$). G.c./m.s. was used to determine the relative conversion. Removal of the dichloromethane under reduced pressure allowed determination of the crude yield.

EXAMPLE 17

Iodination in a Variety of Acids

A solution containing α,α,α-trifluoromethylbenzene (20.1 g, 137.5 mmol) and iodine (21.9 g, 86.2 mmol) in the required acid (150 ml) was placed in the fluorination apparatus. Elemental fluorine (165 mmol) as a 10% mixture in nitrogen was then passed through the stirred solution at ca. 40 ml min$^{-1}$. After the fluorination the mixture was poured into a 5% solution of sodium metabisulfite in ice (1500 ml), extracted with dichloromethane (3×100 ml) and then dried (MgSO$_4$). G.c./m.s. was used to determine the relative conversion.

3. Brominations

The following general procedure was used in Examples 18 to which follow.

A solution containing an aromatic compound to be brominated and bromine in sulfuric acid (150 ml) was placed in a fluorination apparatus fitted with a soda lime scrubber. Elemental fluorine (165 mmol) as a 10% mixture in nitrogen was then passed through the stirred solution at ca. 40 ml min$^{-1}$. After the passage of fluorine the solution was poured into a approximate 5% mixture of sodium metabisulfite in ice and extracted with dichloromethane (3×100 ml) which was then dried (MgSO$_4$). The dichloromethane was removed under vacuum leaving a solid or oil which was then purified by recrystallisation from ethanol or distilled to afford a pure product.

EXAMPLE 18

4-Bromo-4-fluoronitrobenzene

4-Fluoronitrobenzene(19.4 g, 137.5 mmol) and bromine (21.2 g, 83.5 mmol) gave 3-bromo-4-fluoronitrobenzene (21.4 g, 58.5%); m.p. 57°–59° C. (lit,[4] 58°–59° C.); (Found: C, 32.6; H, 1.31; N, 6.14. $C_6H_3BrFNO_2$ requires C, 32.9; H, 1.37; N, 6.39%); $\delta_H$ 7.3 (1H, dd, $^3J_{H-H}$ 7.4, $^3J_{H-F}$ 9.1, 5-H), 8.2 (1H, ddd, $^3J_{H-H}$ 9.0, $^4J_{H-H}$ 2.8, $^4J_{H-F}$ 4.1, 6-H) and 8.5 (1H, dd, $^4J_{H-H}$ 2.7, $^4J_{H-F}$ 5.8, 2-H); $\delta_F$ −96.0 (1F, ddd, $^3J_{F-H}$ 7.3, $^4J_{F-H}$ 5.9, $^4J_{F-H}$ 4.1, 4-F); $\delta_C$ 110.1 (1C, d, $^2J_{C-F}$ 23.5, 3-C), 117.1 (1C, d, $^2J_{C-F}$ 24.6, 5-C), 124.9 (1C, d, $^3J_{C-F}$ 9.1, 6-C), 128.3 (1C, s, 1-C), 129.6 (1C, d, $^3J_{C-F}$ 2.2, 1-C) and 162.9 (1C, d, $^1J_{C-F}$ 258.3, 4-C); m/z (EI$^+$) 221 (M$^+$, 46.8%) and 219 (M$^+$, 55.1%).

EXAMPLE 19

5-Bromo-2,4-Difluoronitrobenzene 2,4-Difluoronitrobenzene(21.9 g, 137.5 mmol) and bromine(21.2 g, 83.5 mmol) gave 5-bromo-2,4-difluoronitrobenzene(21.2 g, 65.4%); b.p. 98° C./8 mm; (Found: C, 30.43; H, 0.83; N, 5.92.$C_6H_2BrF_2NO_2$ requires C, 30.38; H, 0.84; N, 5.91%); $\delta_H$ 7.2 (1H, dd, $^3J_{H-F}$ 7.8, $^3J_{H-F}$ 10.3, 3-H) and 8.4 (1H, t,$^4J_{H-F}$ 7.4, 6-H); $\delta_F$ −91.2 (1F, ddd, $^3J_{F-H}$ 14.3, $^4J_{F-H}$ 7.9, $^4J_{F-H}$ 7.1, 2-F) and −112.0 (1F, ddd, $^3J_{F-H}$ 14.3, $^4J_{F-H}$ 10.2, $^4J_{F-H}$ 7.9, 4-F); $\delta_C$ 104.7 (1C, dd, $^2J_{C-F}$ 23.5, $^4J_{C-F}$ 4.5, 5-C), 107.6 (1C, t, $^2J_{C-F}$ 27.4, 3-C), 129.1 (1C, s, 1-C), 131.0 (1C, t, $^3J_{C-F}$ 2.5, 6-C), 155.7 (1C, dd, $^1J_{C-F}$ 268.7, $^3J_{C-F}$ 11.8, 2-C) and 162.4 (1C, dd, $^1J_{C-F}$ 260.3, $^3J_{C-F}$ 11.4, 4-C); m/z (EI$^+$) 239 (M$^+$, 23.8%) and 237 (M$^+$, 24.1).

EXAMPLE 20

3-Bromo-4-fluorobenzoic Acid

4-Fluorobenzoic acid(19.3 g, 137.5 mmol) and bromine (21.2 g, 83.5 mmol) gave 3-bromo-4-fluorobenzoic acid (16.8 G, 65%); m.p. 137°–139° C. (lit,[5] 138°–140° C.); (Found: C, 38.46; H, 1.64: N, 0. $C_7H_4BrFO_2$ requires C, 38.53; H, 1.8; N, 0%); $\delta_H$ 7.2 (1H, dd, $^3J_{H-F}$ 8.4, $^3J_{H-H}$ 8.4, 5-H), 8.1 (1H, ddd, $^3J_{H-H}$ 4.7, $^4J_{H-F}$ 4.3, $^4J_{H-H}$ 2.1, 6-H) and 8.4 (1H, dd, $^4J_{H-F}$ 6.6, $^4J_{H-H}$ 2.1, 2-H); $\delta_F$ −98.0 (1F, ddd, $^3J_{F-H}$ 8.3, $^3J_{F-H}$ 6.8, $^4J_{F-H}$ 4.9, 4-F); $\delta_C$ 110.1 (1C, d, $^2J_{C-F}$ 21.6, 3-C), 117.2 (1C, d, $^2J_{C-F}$ 23.1, 2-C), 127.2 (1C, s, 1-C), 132.0 (1C, d, $^3J_{C-F}$ 8.8, 6-C), 136.6 (1C, dd, $^3J_{C-F}$ 1.9, 2-C), 163.2 (1C, dd, $^1J_{C-F}$ 256.3, 4-C) and 170.8 (1C, s, C=O); m/z (EI$^+$) 220 (M$^+$, 99.5%) and 218 (M$^+$, 100%).

EXAMPLE 21

2-Bromo-4,6-dinitrofluorobenzene 2,4-Difluoronitrobenzene(25.4 g, 137.5 mmol) and bromine(21.2 g, 83.5 mmol) gave 2-bromo4,6-dinitrofluorobenzene(21.8 g, 60.0%); (Found: C, 27.34; H, 0.68: N, 10.41. $C_6H_2BrFN_2O_4$ requires C, 27.3; H, 0.76; N, 10.6%); $\delta_H$ 9.0 (2H, m, 3-H, 5-H); $\delta_F$ −99.8 (1F, s, 1-F); $\delta_C$ 113.7 (1C, d, $^2J_{C-F}$ 22.9, 2-C); 121.7 (1C, s, 5-C), 134.2 (1C, s, 3-C), 137.9 (1C, d, $^3J_{C-F}$ 10.3, 6-C), 143.7 (1C, d, $^4J_{C-F}$ 4.6, 4-C) and 156.6 (1C, d, $^1J_{C-F}$ 273.0, 4-C); m/z (EI$^+$) 266 (M$^+$, 36.8%) and 264 (M$^+$, 38.5%).

4. Chlorination

EXAMPLE 22

Cholorination of Nitrobenzene

A solution of nitrobenzene (16.9 g, 137.5 mmol) and iodine monochloride (26.8 g, 82.5 mmol) and sulphuric acid (100 ml) was placed in a fluorination apparatus with attached soda lime filled drying tube. Elemental fluorine (165 mmol) as a 10% mixture in nitrogen was then passed through the stirred solution using a narrow bore PTFE (polytetrafluoroethylene) tube at a rate of about 40 ml/min. After the fluorine had been added the solution was poured into a 5% solution of sodium metabisulfite (150 ml) extracted with dichloromethane (3×100 ml) and then dried (MgSo$_4$). The dichloromethane was removed under vacuum to leave a red liquid (22 g). Analysis by g.c/m.s. showed a 100% conversion from nitrobenzene to two major products and confirmed them as 3-choloronitrobenzene (44%) m/z (EI$^+$) 159 (M$^+$, 20.0%), 157 (M$^+$, 61.2%) and 3-iodonitrobenzene (45%) m/z (EI$^+$) 249 (MI$^+$, 100%), 203 (M$^+$ —NO$_2$).

5. Use of Interhalogens

EXAMPLE 23

Iodination and chlorination of nitrobenzene

A solution of nitrobenzene (16.9 g, 137.5 mmol), iodine monochloride (26.8 g, 82.5 mmol) and sulfuric acid (150 ml) was placed in a fluorination apparatus with attached soda lime filled drying tube. Elemental fluorine (165 mmol) as a 10% mixture in nitrogen was then passed through the stirred solution at ca. 10 ml min$^{-1}$. After the fluorine has been added the solution was poured into a 5% solution of sodium metabsulfite (1500 ml), extracted with dichloromethane (3×100 ml) and then dried (MgSO$_4$). The dichloromethane was removed under vacuum to leave a red liquid (22 g). Analysis by g.c./m.s. showed a 100% conversion from nitrobenzene to two major products and confirmed then as 3-chloronitrobenzene (44%) m/z (EI$^+$) 159 (M+, 20.0%), 157 (M$^+$, 100%), 203 (M$^+$ —NO$_2$).

What is claimed is:

1. A method of halogenating an aromatic compound which comprises the steps of reacting said aromatic compound in the presence of fluorine with one or more halogenating agents and an acid, wherein said halogenating agent is selected from the group consisting of an iodinating agent, a brominating agent, and a chlorinating agent.

2. A method as in claim 1 wherein said halogenating agent comprises an element selected from the group consisting of elemental iodine, elemental bromine, and elemental chlorine.

3. A method as in claim 1 wherein said halogenating agent comprises at least one interhalogen compound.

4. A method as in claim 1 wherein the fluorine is present together with an inert gas.

5. A method as in claim 1 wherein said aromatic compound is present in a solvent.

6. A method as in claim 1 wherein said method is carried out in the presence of a solvent for fluorine.

7. The method of claim 1, wherein said acid is an organic acid.

8. The method of claim 7, wherein said organic acid is a carboxylic acid.

9. The method of claim 8, wherein said carboxylic acid comprises at least one of formic acid, acetic acid and trifluoroacetic acid.

10. The method of claim 1, wherein said acid is an inorganic acid.

11. The method of claim 10, wherein said inorganic acid comprises at least one of sulphuric acid, trifluoromethanesulphonic acid, fluorosulphuric acid, hydrogen fluoride and antimony pentafluoride/hydrogen fluoride.

12. The method of claim 1, wherein said method is carried out at ambient temperature.

13. A method of halogenating an aromatic compound which comprises the steps of reacting said aromatic compound in the presence of fluorine with one or more halogenating agents and an acid.

14. The method of claim 13, wherein said halogenating agent is selected from the group consisting of an iodinating agent, a brominating agent, and a chlorinating agent.

15. The method of claim 13, wherein said method is carried out at ambient temperature.

16. The method of claim 13, wherein said acid comprises at least one of carboxylic acid, sulphuric acid, trifluoromethanesulphonic acid, fluorosulphuric acid, hydrogen fluoride and antimony pentafluoride/hydrogen fluoride.

17. The method of claim 16, wherein said carboxylic acid comprises at least one of formic acid, acetic acid and trifluoroacetic acid.

18. A method of halogenating an aromatic compound at ambient temperature which comprises the steps of reacting said aromatic compound in the presence of fluorine with one or more halogenating agents and an acid, wherein said halogenating agent is selected from the group consisting of elemental iodine, elemental bromine, and elemental chlorine; and said acid comprises at least one of a formic acid, acetic acid, trifluoroacetic acid, sulphuric acid, trifluoromethanesulphonic acid, fluorosulphuric acid, hydrogen fluoride and antimony pentafluoride/hydrogen fluoride.

\* \* \* \* \*